United States Patent [19]

Stouder, Jr.

[11] Patent Number: 5,350,362
[45] Date of Patent: Sep. 27, 1994

[54] SELECTABLE SEAL CANNULA

[76] Inventor: Albert E. Stouder, Jr., 318 N. West, Tipton, Ind. 46072

[21] Appl. No.: 62,992

[22] Filed: May 18, 1993

Related U.S. Application Data

[63] Continuation-in-part of Ser. No. 903,370, Jun. 24, 1992, Pat. No. 5,211,633.

[51] Int. Cl.$^5$ .............................................. A61M 5/178
[52] U.S. Cl. .................................. 604/167; 604/247; 604/264
[58] Field of Search ............... 604/167, 169, 256, 283, 604/164, 247, 237, 264

[56] References Cited

U.S. PATENT DOCUMENTS

| | | |
|---|---|---|
| 4,000,739 | 1/1977 | Stevens . |
| 4,177,814 | 12/1979 | Knepshield et al. . |
| 4,177,814 | 12/1979 | Knepshield et al. . |
| 4,655,752 | 4/1987 | Honkanen et al. . |
| 4,895,346 | 1/1990 | Steigerwald . |
| 4,895,565 | 1/1990 | Hillstead . |
| 4,909,798 | 3/1990 | Fleischhacker et al. . |
| 5,020,543 | 6/1991 | Rothenberg et al. . |
| 5,041,097 | 8/1991 | Johnson . |
| 5,092,857 | 3/1992 | Fleischhacker . |

OTHER PUBLICATIONS

Two photographs of an Originsingle use surgical trocar and sleeve, with accompanying photocopy of package insert, of Origin Medsystems, Inc., San Carlos, Calif.
Two photographs of a Trocan TM 5 mm Disposable Surgical Trocar and Cannula (reorder No. 004536-901) of Cabot Medical Corporation, Langhorne, Pa., which is marked on its packaging with the above-cited U.S. Pat. No. 4,177,814, with accompanying photocopy of reverse side of packaging for such trocar and cannula.

Primary Examiner—John D. Yasko
Attorney, Agent, or Firm—Woodard, Emhardt, Naughton, Moriarty & McNett

[57] ABSTRACT

A surgical cannula having selectable gaskets which assure a fluid-tight seal around medical devices of a variety of sizes. The cannula includes a tubular member insertable into a medical patient, a two-piece housing mounted to the proximal end of the tubular member, and a movable member mounted to the housing and selectively movable between a first position and a second position across the passage. The movable member has at least two apertures through which surgical instruments may be passed.

A first gasket is included in the two-piece housing to seal around the largest instruments passed through the cannula. A second gasket is included in the movable member to provide a fluid-tight seal when smaller instruments are used. When the movable member is in its first position a gasketless aperture in the movable member is aligned with the lumen of the tubular member to accommodate large medical instruments. When the movable member is in its second position the second gasket is aligned with the lumen to provide a fluid-tight seal around the second medical device.

23 Claims, 12 Drawing Sheets

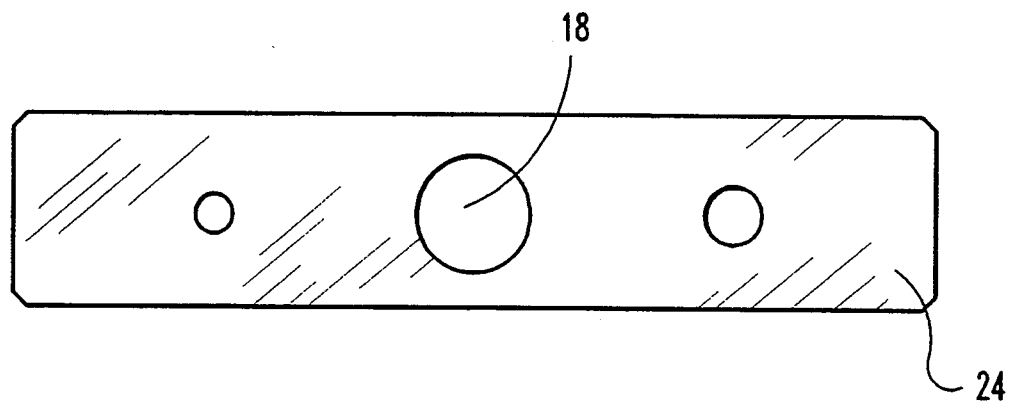
Fig. 7
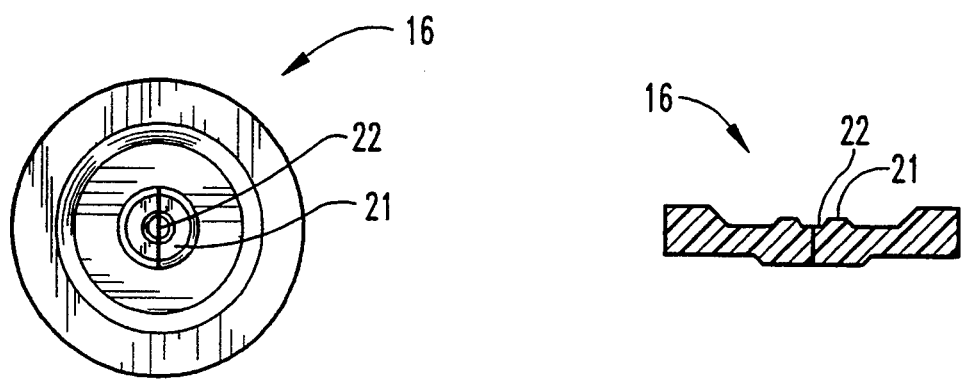
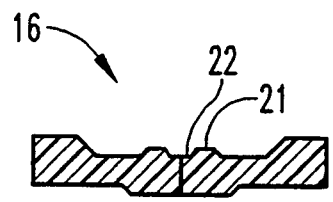
Fig. 9
Fig. 8
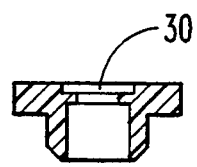
Fig. 10

SELECTABLE SEAL CANNULA

REFERENCE TO RELATED APPLICATIONS

This application is a continuation-in-part to my co-pending patent application Ser. No. 07/903,370, filed Jun. 24, 1992, issued as U.S. Pat. No. 5,211,633 on May 18, 1993.

BACKGROUND OF THE INVENTION

This invention relates generally to surgical cannulas, and more particularly to a laparoscopic cannula which provides a fluid-tight seal around laparoscopic instruments of various outer diameters.

In medical procedures such as laparoscopy the patient's abdomen is distended to allow access to and visibility of the abdominal cavity. In order to distend the abdominal cavity a gas is injected into the cavity at a pressure of about 12 torr. The gas insufflates the abdominal cavity, supporting the abdominal walls up and away from the internal organs. Without this maintained pressure the abdominal wall collapses and all visibility through the laparoscopic camera is lost.

While the abdomen is distended with gas, cannulas through which medical instruments can be inserted traverse the abdominal wall. Valves are typically included in these cannulas to prevent air from leaking from the pressurized cavity when the laparoscopic cannula is in use. The competence of these valves is of great importance because even a small leak in the cannula may cause a decrease in insufflation pressure and the attendant collapse of the abdominal wall.

A variety of laparoscopic instruments are used with such cannulas. For example, laparoscopic forceps, clamps, scalpels, etc., are all known. These laparoscopic instruments are typically round in cross section, and have outer diameters ranging from about 2 mm to about 1 cm. In many laparoscopic procedures it is necessary to remove a larger laparoscopic instrument and to replace it with a smaller instrument during the course of the procedure. It is not practical to replace the cannula at such times.

Laparoscopic cannulas are available with lumen diameters of 5 mm, 1 cm, etc., with the larger sizes being preferred for laparoscopic procedures in which larger-diameter laparoscopic instruments may be required. The valve employed in the cannula may be any valve which seals around medical instruments, such as a slit valve, etc. However, all single-valve systems are known to leak when the smallest laparoscopic instruments are used in large-lumened cannulas.

Presently, the insertion of small instruments into the 1 cm or larger cannulas requires a reducing gasket to prevent significant air loss. In the larger cannulas of the prior art, such as the TROCAN ™ 5 mm Disposable Surgical Trocar and Cannula No. 004536-901, the reducing gasket is a plastic cap which is inserted over the outer opening of the cannula to reduce the effective size of the opening. It can be appreciated that changing the reducing gasket is a time-consuming inconvenience to the medical team since the gasket must pass from the nurse to the doctor before being applied to the cannula. The time and effort required to change prior art gaskets is an undesirable aspect of such devices.

A need therefore exists for a universal cannula which may rapidly be adapted to accept laparoscopic instruments of varying sizes and to provide a fluid-tight seal around such instruments. The present invention addresses this need. Furthermore, the present invention has applicability in other surgical procedures such as cardiological procedures involving inserting guide wires, catheters and other medical devices into a medical patient's blood vessels or other body cavities.

SUMMARY OF THE INVENTION

Briefly describing the present invention, there is provided a surgical cannula having selectable gaskets which assure a fluid-tight seal around medical devices of a variety of sizes. The cannula includes a tubular member insertable into a medical patient, a two-piece housing mounted to the proximal end of the tubular member, and a movable member mounted to the housing and selectively movable between a first position and a second position across the passage. The movable member has at least two apertures through which surgical instruments may be passed.

A first gasket is included in the two-piece housing to seal around the largest instruments passed through the cannula. A second gasket is included in the movable member to provide a fluid-tight seal when smaller instruments are used. When the movable member is in its first position a gasketless aperture in the movable member is aligned with the lumen of the tubular member to accommodate large medical instruments. When the movable member is in its second position the second gasket is aligned with the lumen to provide a fluid-tight seal around the second medical device.

The present invention also provides a method of using a surgical cannula having a movable member with selectable seals to assure a fluid-tight interface when the cannula is used in combination with various sized medical devices.

One object of the present invention is to provide a cannula which provides a fluid-tight seal when used with medical instruments having a wide range of outer diameters.

Another object is to provide an improved surgical cannula.

A further object of the present invention is to provide a method of using a selectable seal cannula.

Related objects and advantages of the present invention will be apparent from the following description.

DESCRIPTION OF THE DRAWINGS

FIG. 7 is a top plan view of the movable member tray cover of the present invention.

FIG. 8 is a top plan view of a valve fixed in the housing of the present invention.

FIG. 9 is a cross-sectional view of the valve of FIG. 8.

FIG. 10 is a cross-sectional view of a gasket used in the movable member of the present invention.

DESCRIPTION OF THE PREFERRED EMBODIMENT

Figure 1:
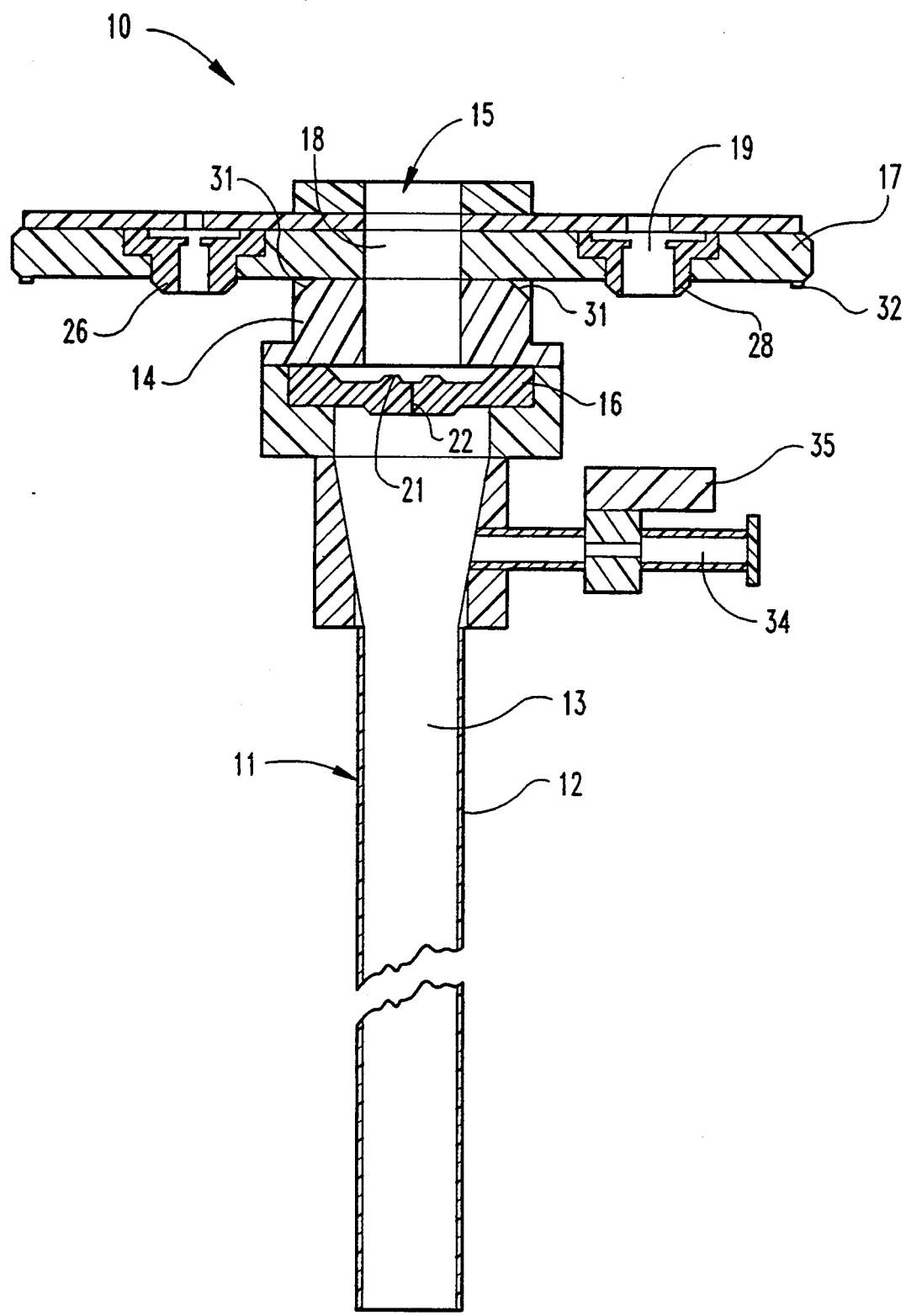
FIG. 1 is a side cross-sectional view of the cannula of the present invention according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and method, and such further applications of the principles of the invention as illustrated herein being contemplated as would normally occur to one skilled in the art to which the invention relates.

Figure 11:
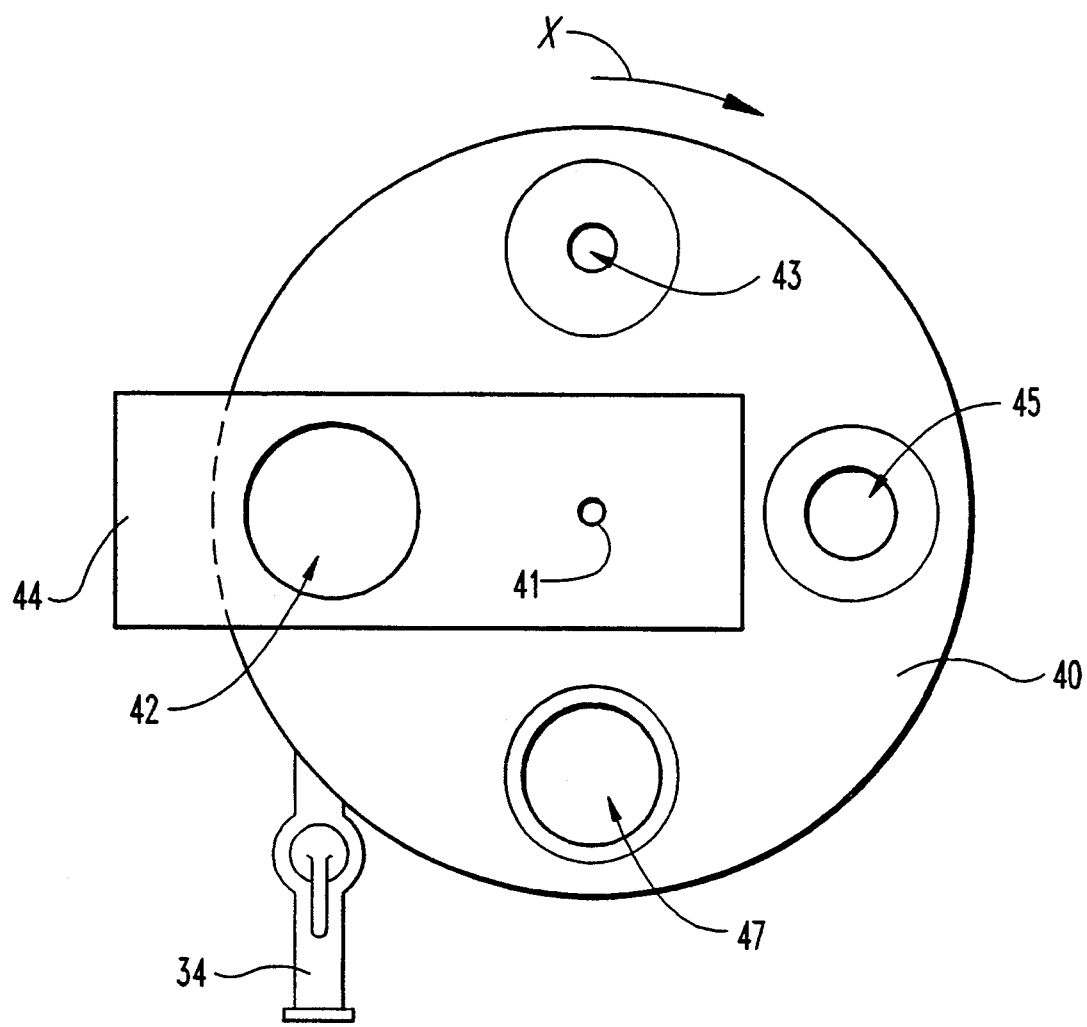
FIG. 11 is a top plan view of an alternative embodiment of the present invention wherein the movable member is rotatably movable with respect to said housing.

Referring now to the drawings, FIGS. 1 through 10 illustrate the universal cannula according to one preferred embodiment, while FIG. 11 illustrates a second embodiment of the device. FIGS. 12 through 18 illustrate the universal cannula according to a third preferred embodiment, including the two-piece housing and the replaceable gasket tray.

Universal cannula 10 includes a tubular member 11 which traverses the abdominal wall and serves as a conduit through which laparoscopic or other medical instruments can be passed. Tubular member 11 may be made of stainless steel or otherwise and includes a side wall 12 defining a lumen 13. The lumen is preferably one centimeter in diameter, although larger or smaller lumen sizes may be used.

A housing 14 is mounted to the proximal end of tubular member 11. Housing 14 includes a passageway 15 aligned with lumen 13 to allow medical instruments to be passed through the cannula. Housing 14 also preferably includes a valve 16 fixed in the passageway to provide an airtight seal around large-diameter laparoscopic instruments when such instruments are used. Fixed valve 16 also prevents air from leaking through the cannula when no laparoscopic instrument is being used.

Concerning specifically fixed valve 16, the design is of the slit valve type. The valve has an offset superior protrusion 21 close to the center 22 of the valve. This helps decrease air leakage when using 5 mm-diameter instruments. When these instruments are passed through the valve the silastic will be pushed downward and the protrusions will effectively make the valve opening smaller. This action snugs the silastic around the 5 mm instrument and decreases the amount of air that escapes through the valve. Note that when using smaller instruments this valve alone may not provide adequate sealing.

Accordingly, additional valves may be provided on movable member 17 mounted to the housing. Movable member 17 is selectively movable between a first position and a second position across passageway 15. When movable member 17 is in its first position (FIGS. 1 and 2), larger-sized medical devices such as instrument M1 having a diameter D1 may be inserted through the cannula as shown in FIG. 2. When movable member 17 is in its second position (FIG. 3), a gasketed aperture 19 with an opening smaller than the passageway is aligned with the lumen so that smaller-sized laparoscopic instrument may be inserted without fluid leaks.

Figure 5:
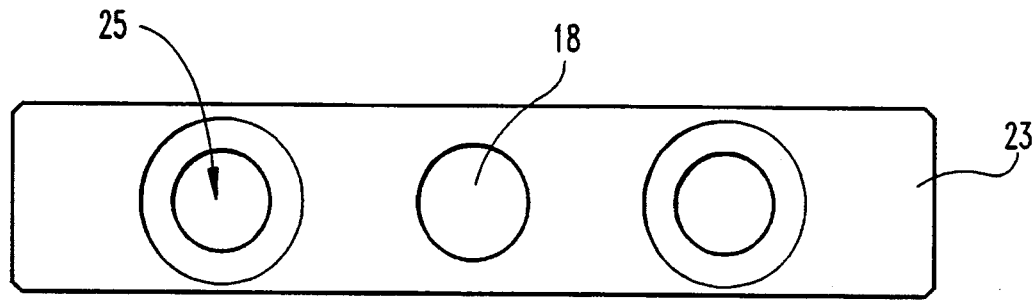
FIG. 5 is a top plan view of one embodiment of the movable member tray of the present invention.
Figure 6:
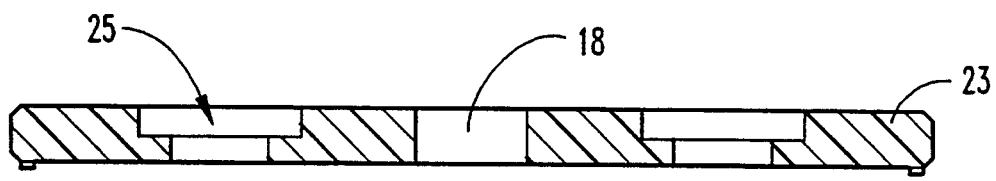
FIG. 6 is a side cross-sectional view of the movable member tray of FIG. 5.

Movable member 17 preferably includes a tray 23, a tray cover 24, non-valved aperture 18 and one or more valves held in respective apertures, such as aperture 25, in the tray (see FIGS. 5 and 6). Each valve preferably comprises a gasket 26 or 28 with an aperture 27 or 29, respectively, which is smaller than the passageway to prevent air loss when small-sized medical instruments are used. Thus, even if fixed valve 16 leaks the smaller valves in the gaskets remain competent, thus maintaining integrity of the system.

The gaskets 26 and 28 used in movable member 17 are preferably silastic gaskets which provide a fluid-tight seal around laparoscopic instruments inserted through the cannula. Preferred gaskets include a constricted portion 30 (see FIG. 10) in the upper portion of the gasket. The constricted portion is preferably slightly smaller than the instruments used so that the gasket forms a seal around the instrument. In addition, the constricted portion assists in minimizing the contact with the laparoscopic instrument so that the frictional force of moving the instrument in and out will not be enough to dislodge the gasket from its sealed position. It is to be understood that any number of valve/gasket configurations may be used, including multiple slits, punctures, multilayered gaskets and the like.

Housing 14 also preferably includes bevels 31 at the edges of the surface across which movable member 17 slides. These bevels serve to assist in pushing the silastic gasket up into the tray when the bottom of the gasket slides through the housing to the passageway. By sliding the tray in either direction the bottom of the gasket will hit the beveled housing. Since the silastic is somewhat compressible, it will bulge into the hole in its center, as well as elevate slightly, as the movable member and gasket slide through the housing toward the passageway. When the gasket is positioned in the passageway the gasket will seat in that opening and by expansion to its usual size will form a seal. A stop, such as stop member 32, may be provided at the ends of the movable member to prevent it from accidentally falling out of the housing.

Although in one embodiment the movable member includes one gasketed aperture and one nongasketed aperture, in alternative embodiments two or more gasketed apertures are provided so that a wider range of laparoscopic or other medical instruments may be used. In preferred embodiments movable member 17 includes three apertures. The center, non-valved aperture 18 is typically a hole which is provided so that large-sized laparoscopic instruments may be inserted into the cannula passageway. For example, aperture 18 may have a diameter D5 (see FIG. 4) of one centimeter which is large enough to accommodate most larger-sized instruments. When the non-valved aperture of movable member 17 is aligned with the passageway, fixed valve 16 prevents air loss and the collapse of the abdominal cavity. The other apertures include gaskets as described above which remain competent against fluid leaks when smaller-diameter instruments are used. For example, first valve gasket 26 may include a gasket to provide a 3 mm diameter D3 aperture 27, while second valve gasket 28 may include a gasket to provide a 5 mm diameter D4 aperture 29. The gasket openings are smaller than passageway 15 (i.e., D3 and D4 are both smaller than D5) and preferably correspond in size to the outer cross sectional dimensions of a small-diameter laparoscopic instruments.

The valve gaskets of the present invention preferably all have a common outer dimension, whereas the inner opening of the gasket varies in size according to its intended use. It is to be appreciated that such valve gaskets may be quickly and easily interchanged, and that any size of inner valve opening may be supplied. Further, the apertures 25 holding the valve gaskets are preferably countersunk to prevent the gasket or valve body used in the aperture from slipping through. While the inner shape and size of the apertures in time valves/gaskets are typically referred to in terms of "diameter", it is to be understood that this term encompasses noncircular shapes of various sizes corresponding to medical instrument to be used.

Figure 2:
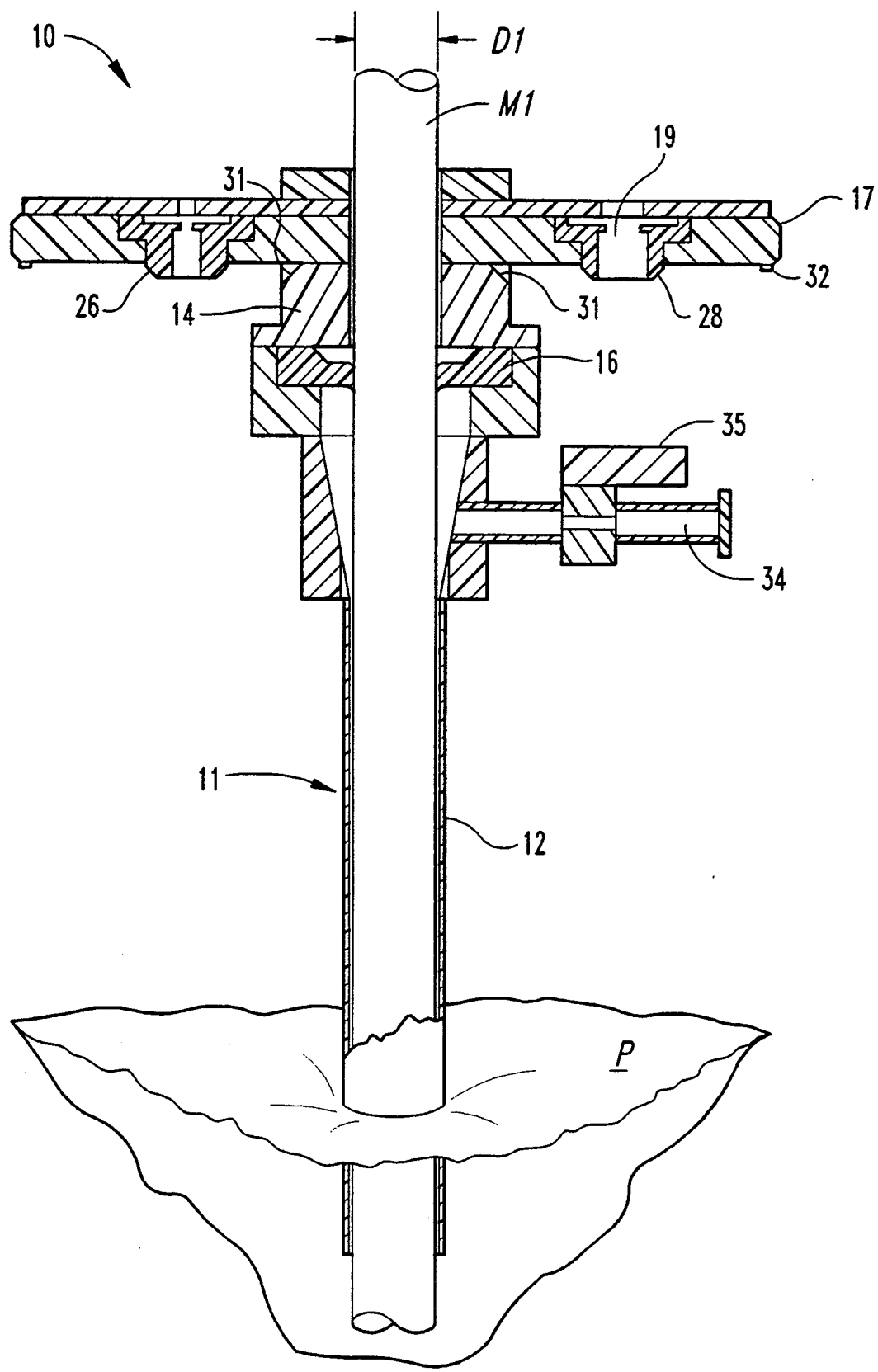
FIG. 2 is a side cross-sectional view of the cannula of FIG. 1 inserted in a medical patient and with a large-sized medical device inserted through the cannula.
Figure 3:
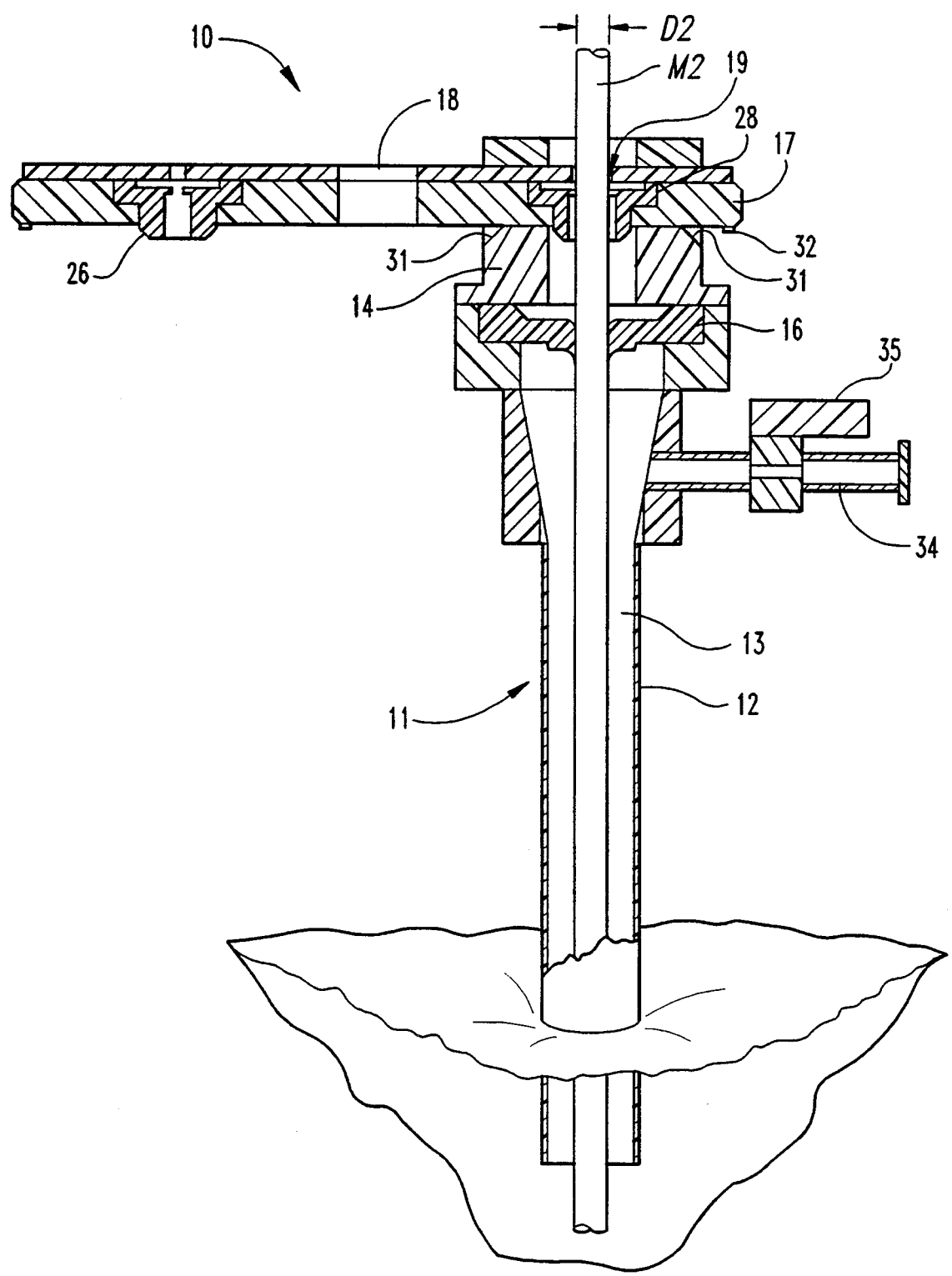
FIG. 3 is a side cross-sectional view of the cannula of FIG. 2 with a smaller-sized medical device inserted through the cannula.
Figure 4:
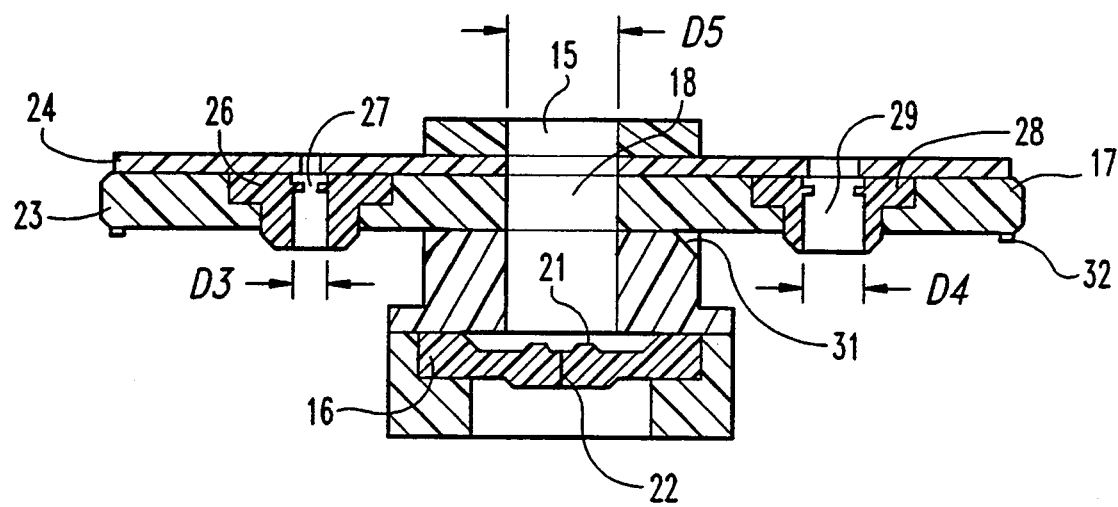
FIG. 4 is a side cross-sectional view of the housing and movable member of the device of FIG. 1.

A side port 34 may also be included in the cannula (see FIGS. 1-3). Side port 34 allows fluids to be supplied or withdrawn through the cannula. Side port 34 may further include a valve 35 to control the flow of fluids through the port. Port 34 is preferably located fluidally between valve 16 and tubular member 11, allowing fluid control through the port even when a medical instrument is removed and valve 16 is closed.

A method of using the cannula of the present invention includes the following steps. First, tubular member 11 is inserted and secured in a medical patient P. A first medical device M1 with a first outer diameter D1 is inserted into the lumen and used as is known to those skilled in the art. After using the first medical device, that device is removed. The movable member of the present invention, including a first valve body, is thereafter positioned so that the first valve body is aligned with the lumen. A second medical device M2 with a second outer diameter D2 is inserted through the first valve body and into the lumen. The opening of the first valve body is smaller than the lumen, so that the first valve body provides a fluid-tight seal around said second medical device.

It is to be appreciated that the movable member need not be a rectangular tray radially slidable across the passageway of the cannula. For example, movable member 40 may be circular, like a wheel or disk, so that the smaller-sized valves are rotatably movable with respect to the housing. As can be seen in FIG. 11, in this embodiment movable member 40 rotates about a pivot 41 somewhat offset from the passageway 42 of a cannula. When movable member 40 is rotatably moved in path X with respect to the housing 44, the apertures 43, 45, 47 and 49 positioned over the cannula passageway can be rapidly and selectively changed. Other embodiments which selectively position a valve member in the passageway of a cannula may also be employed such as a transversely slidable arcuate-shaped tray movable in an arcuate path.

Referring now to FIGS. 12-20, most components are similar to the corresponding components in FIGS. 1-10. Universal cannula 110 includes a tubular member 111 which traverses the abdominal wall and serves as a conduit through which laparoscopic or other medical instruments can be passed. Tubular member 111 may be made of stainless steel or otherwise and includes a side wall 112 defining a lumen 113. Here too, the lumen is preferably one centimeter in diameter, although larger or smaller lumen sizes may be used.

A two-piece housing 114 mounted to the proximal end of tubular member 111 is a distinguishing feature of cannula 110. Housing 114 includes upper housing member 114a and lower housing member 114b, which together define a passageway 115 aligned with lumen 113 to allow medical instruments to be passed through the cannula. Housing 114 also preferably includes a valve 116 fixed in the passageway to provide an airtight seal around large-diameter laparoscopic instruments when such instruments are used. Fixed valve 116 also prevents air from leaking through the cannula when no laparoscopic instrument is being used.

The design is of fixed valve 116 is again of the slit valve type. The valve has an offset superior protrusion 121 close to the center 122 of the valve to help decrease air leakage when using 5 mm-diameter instruments. When these instruments are passed through the valve the silastic will be pushed downward and the protrusions will effectively make the valve opening smaller. This action snugs the silastic around the 5 mm instrument and decreases the amount of air that escapes through the valve. When using smaller instruments this valve alone may not provide adequate sealing.

The two-piece housing allows the removal and replacement of fixed valve 116. Accordingly, upper housing member 114a and lower housing member 114b are constructed to interface at fixed valve 116 so that when the two housing members are separated fixed valve 116 may be easily removed. Members 114a and 114b provide an annular seat in which valve 116 is held in compression therebetween.

Means for mounting the upper housing member 114a to lower housing member 114b are also provided. Because in the preferred embodiment the housing members are joined by screwing the two housing members together, the preferred means for mounting the upper housing to the lower housing comprises cooperating threads 114c in the two housing members. Alternatively, snap-in, bayonet, friction-fit or other means for connecting the housing members may be used with the present invention.

Figure 12:
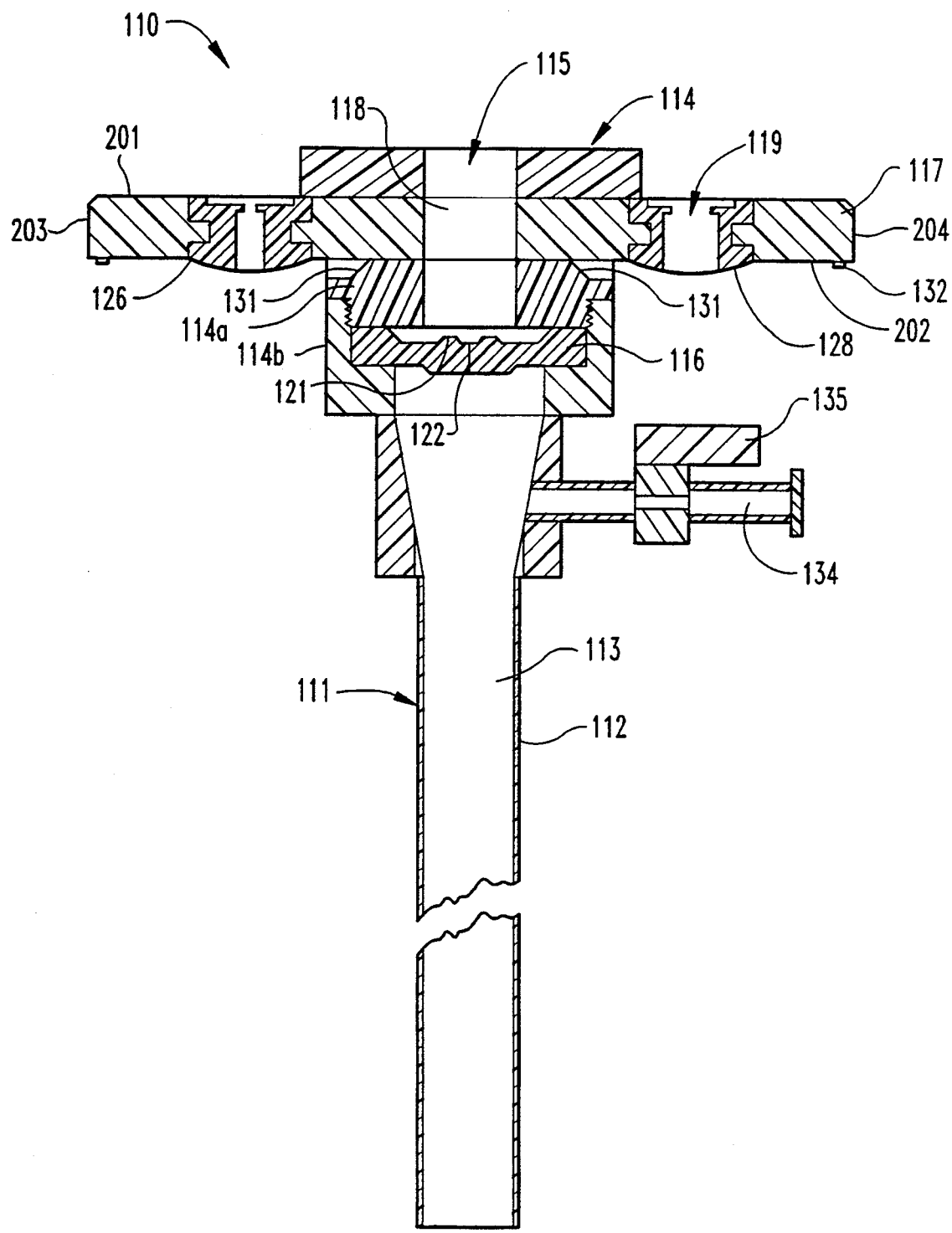
FIG. 12 is a side cross-sectional view of the cannula of the present invention according to one embodiment.
Figure 13:
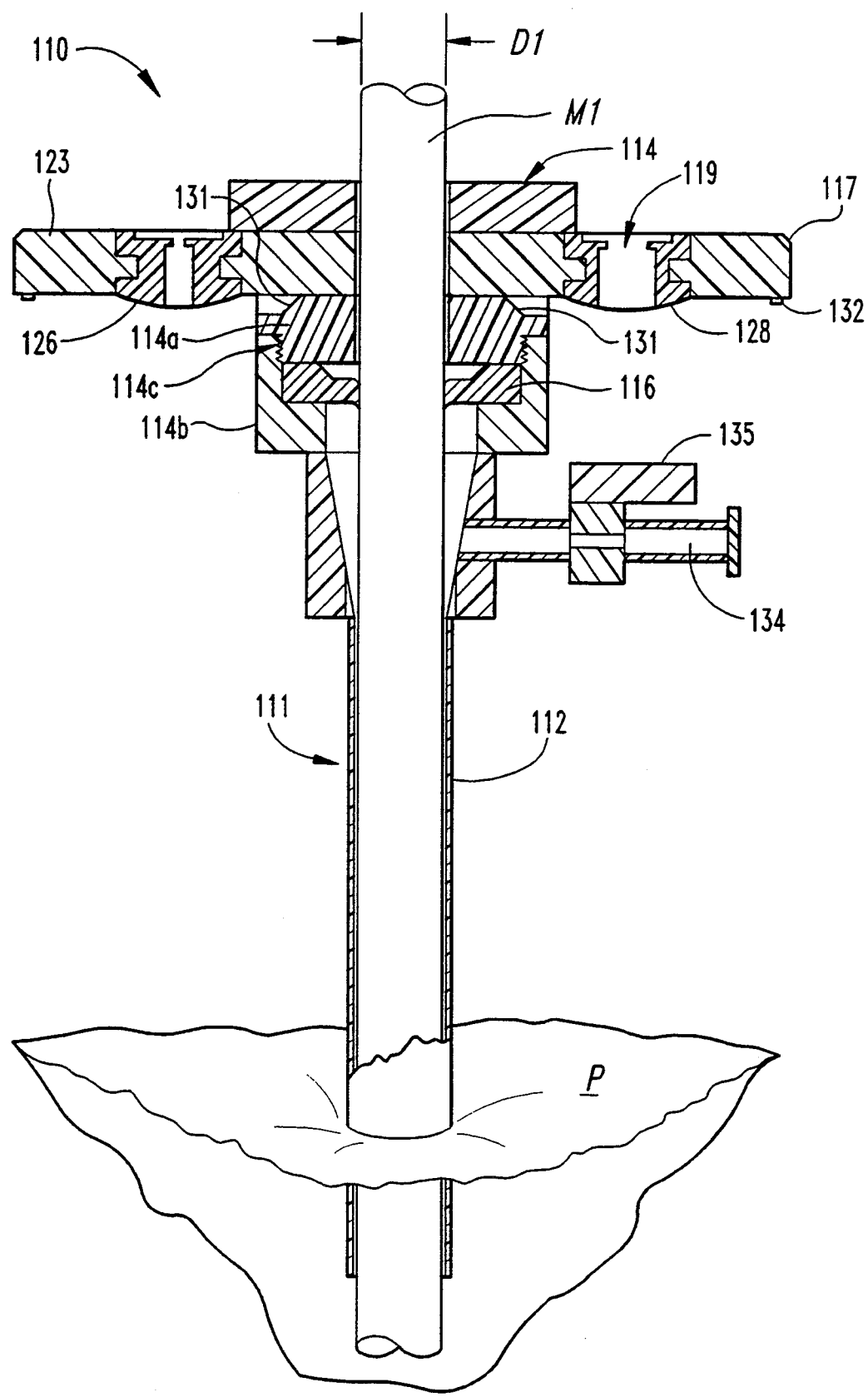
FIG. 13 is a side cross-sectional view of the cannula of FIG. 12 inserted in a medical patient and with a large-sized medical device inserted through the cannula.
Figure 14:
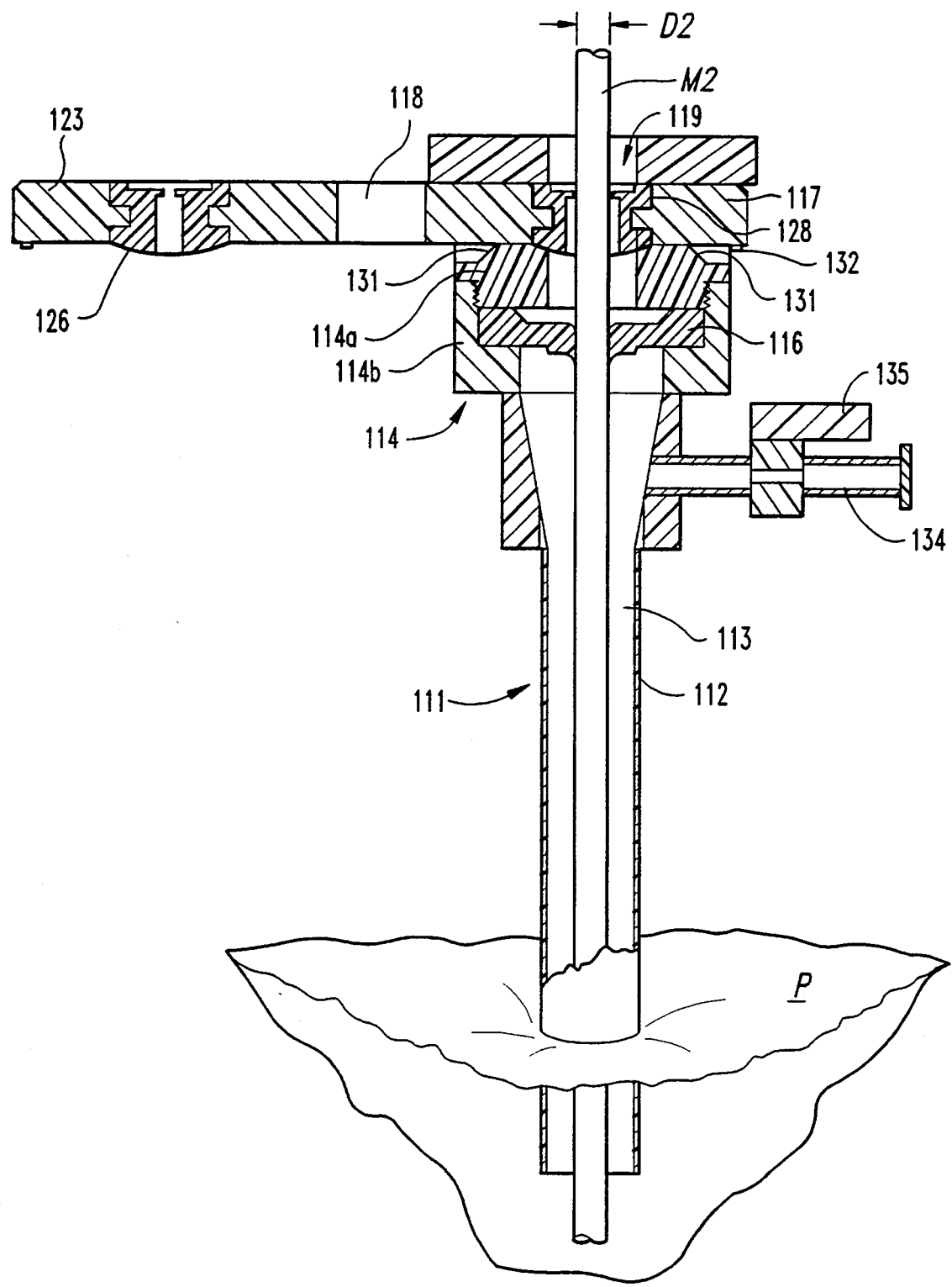
FIG. 14 is a side cross-sectional view of the cannula of FIG. 13 with a smaller-sized medical device inserted through the cannula.
Figure 15:
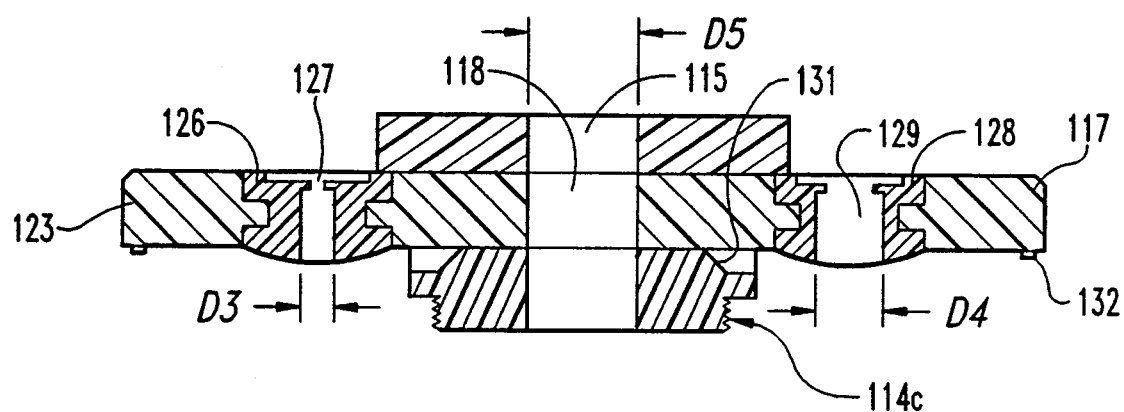
FIG. 15 is a side cross-sectional view of the housing and movable member of the device of FIG. 12.
Figure 16:
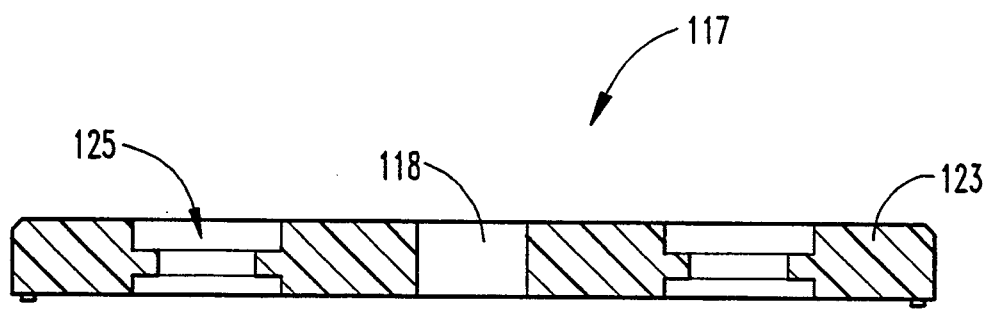
FIG. 16 is a side cross-sectional view of the movable member tray of FIG. 15.
Figure 17:
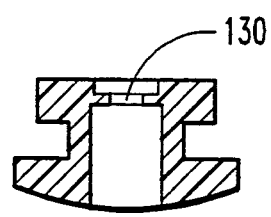
FIG. 17 is a cross-sectional view of a gasket used in the movable member of the present invention.

Additional valves are again preferably provided on movable member 117 mounted to the housing. Movable member 117 is selectively movable between a first position and a second position across passageway 115. When movable member 117 is in its first position (FIGS. 12 and 13), larger-sized medical devices such as instrument M1 having a diameter D1 may be inserted through the cannula as shown in FIG. 12. When movable member 117 is in its second position (FIG. 14), a gasketed aperture 119 with an opening smaller than the passageway is aligned with the lumen so that smaller-sized laparoscopic instrument may be inserted without fluid leaks.

Movable member 117 preferably comprises a tray 123, non-valved aperture 118 and one or more valved apertures in the tray. Each valve preferably comprises a gasket 126 or 128 with an aperture 127 or 129, respectively, which is smaller than the passageway to prevent air loss when small-sized medical instruments are used. Thus, even if fixed valve 116 leaks the smaller valves in the gaskets remain competent, thus maintaining integrity of the system.

The gaskets 126 and 128 used in movable member 117 are preferably silastic or other elastomeric gaskets which provide a fluid-tight seal around laparoscopic instruments inserted through the cannula. Preferred gaskets include a constricted portion 130 (see FIG. 17) in the upper portion of the gasket. The constricted portion is preferably slightly smaller than the instruments used so that the gasket forms a seal around the instrument. In addition, the constricted portion assists in minimizing the contact with the laparoscopic instrument so that the frictional force of moving the instrument in and out will not be enough to dislodge the gasket from its sealed position. As was the case with the other embodiments, any number of valve/gasket configurations may be used, including multiple slits, punctures, multilayered gaskets and the like.

In one preferred embodiment the movable member tray has an oval-shaped upper surface 201 and an oval-shaped lower surface 202, with the upper surface having a smaller surface area than the lower surface. This facilitates rapid identification of the appropriate orientation of the tray, and assures proper insertion of the tray into the housing.

Figure 18:
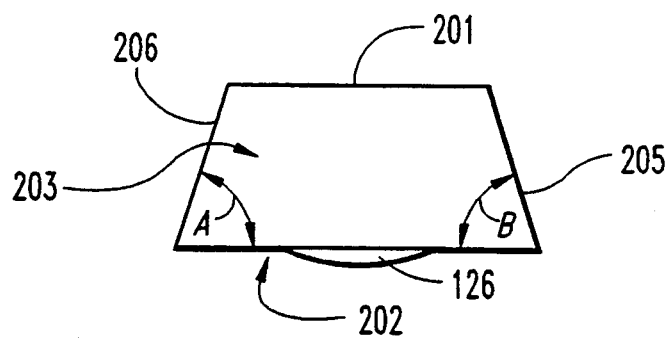
FIG. 18 is an end view of one preferred embodiment of the movable member of the present invention.

In the most preferred embodiments the tray member has a trapezoidal-shaped appearance when viewed from either end or in cross section as shown in FIG. 18. Accordingly, tray member 117 includes an upper surface 201, a lower surface 202, a first end surface 203, a second end surface 204, a side surface 205 and a side surface 206. Preferably, side surface 206 and lower surface 202 define an acute angle A which may be equal to acute angle B (e.g. 60°) formed by side surface 205 and lower surface 202.

Housing 114 has its lateral passage way 117a (perpendicular to the cannula) (see FIG. 19) in which the trapezoidal-shaped member slides similarly and correspondingly trapezoidal-shaped to receive the tray member therein. Such corresponding shape provides good fluid sealing and, as indicated, prevents improper inverting of the tray in the passage way.

Housing 114 also preferably includes bevels 131 at the edges of the surface across which movable member 117 slides. These bevels serve to assist in pushing the silastic gasket up into the tray when the bottom of the gasket slides through the housing to the passageway. By sliding the tray in either direction the bottom of the gasket will hit the beveled housing. Since the silastic is somewhat compressible, it will bulge into the hole in its center, as well as elevate slightly, as the movable member and gasket slide through the housing toward the passageway. When the gasket is positioned in the passageway the gasket will seat in that opening and by expansion to its usual size will form a seal. A stop, such as stop member 132, may be provided at the ends of the movable member to prevent it from accidentally falling out of the housing.

Alternative embodiments having two or more gasketed apertures may also be provided so that a wider range of laparoscopic or other medical instruments may be used. In the most preferred embodiments movable member 117 includes three apertures. The center, non-valved aperture 118 is typically a hole which is provided so that large-sized laparoscopic instruments may be inserted into the cannula passageway. For example, aperture 118 may have a diameter D5 of one centimeter which is large enough to accommodate most larger-sized instruments. When the non-valved aperture of movable member 117 is aligned with the passageway, fixed valve 116 prevents air loss and the collapse of the abdominal cavity. The other apertures include gaskets as described above which remain competent against fluid leaks when smaller-diameter instruments are used. For example, first valve gasket 126 may include a gasket to provide a 3 mm diameter D3 aperture 127, while second valve gasket 128 may include a gasket to provide a 5 mm diameter D4 aperture 129. The gasket openings are smaller than passageway 115 (i.e., D3 and D4 are both smaller than D5) and preferably correspond in size to the outer cross sectional dimensions of a small-diameter laparoscopic instruments.

The valve gaskets of the present invention preferably all have a common outer dimension, whereas the inner opening of the gasket varies in size according to its intended use. It is be appreciated that such valve gaskets may be quickly and easily interchanged, and that any size of inner valve opening may be supplied. Further, the apertures 125 holding the valve gaskets are preferably countersunk on both the top and bottom surfaces of the gasket tray to prevent the gasket or valve body used in the aperture from being pushed or pulled through.

In preferred embodiments the valve gaskets include upper and lower flanges which match the countersunk apertures. Most preferably, the flange at the bottom of the gasket will be larger than the flange at the top to prevent time gasket from being pushed through the aperture when insufflation pressure is applied. The upper and lower flanges also prevent the gasket from becoming dislodged when a medical instrument is being passed through the gasket.

Figure 21:
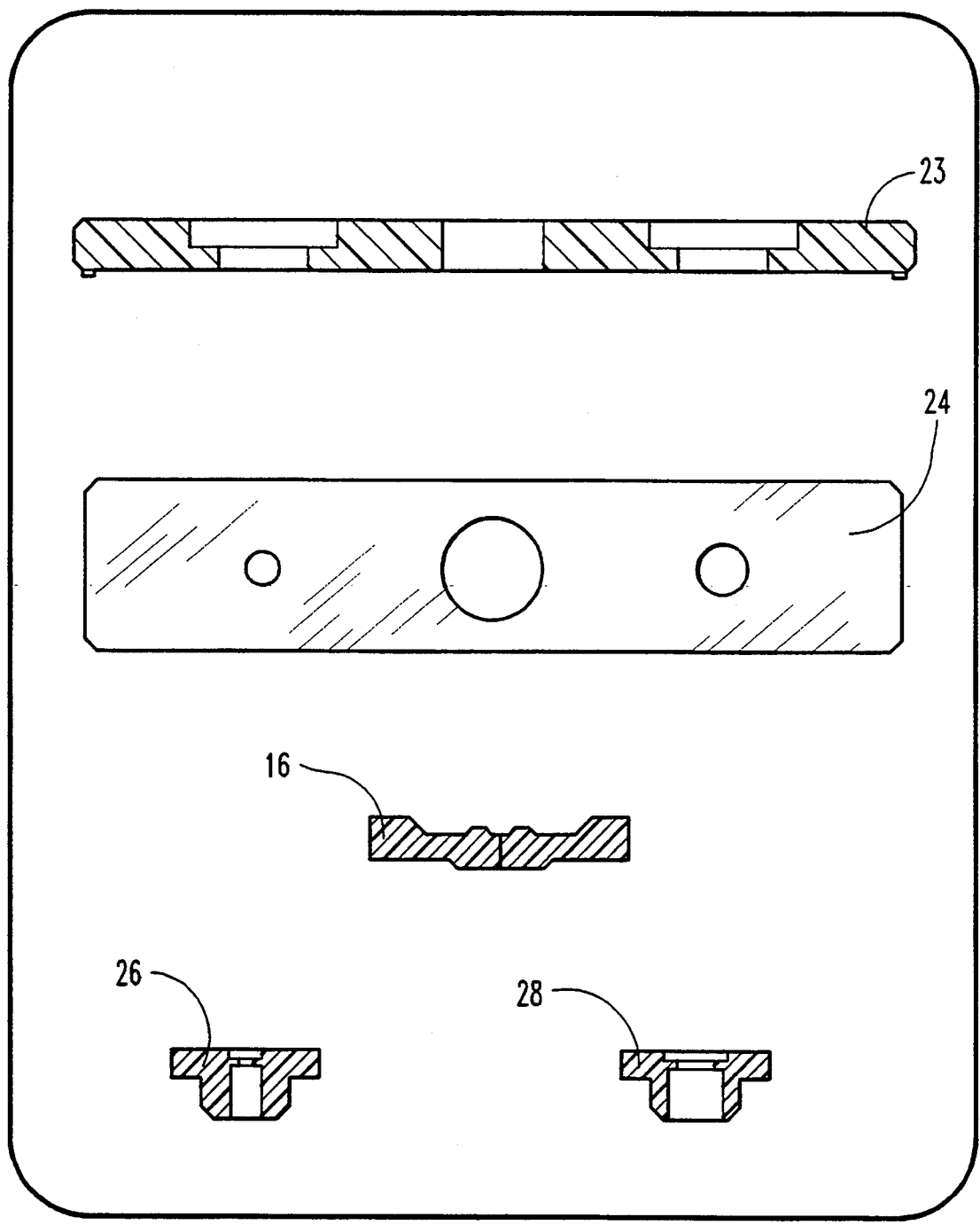
FIG. 21 shows the movable member of the present invention provided as a kit, according to one preferred embodiment.

The movable member of the present invention may also be provided as a kit. Thus, the gasket tray may be replaced to assure appropriate sterilization of the gaskets and other critical components. In one preferred embodiment a kit K (See FIG. 21) having a gasket tray with gaskets therein, and a separate gasket for insertion into the two-piece housing is provided. The gasket tray and all gaskets included in the kit are provided in surgically sterile form as appropriate for surgical use. The kit preferably comes in an outer package to maintain sterility, and more preferably in a package which allows in-packaging sterilization as is known.

It is to be appreciated that when the gasket components are provided as a kit the costs associated with the device are desirably decreased. With the cannula kit, only the relatively inexpensive kit components are replaced for each use, with the main portion of the cannula being sterilized for reuse.

Figure 19:
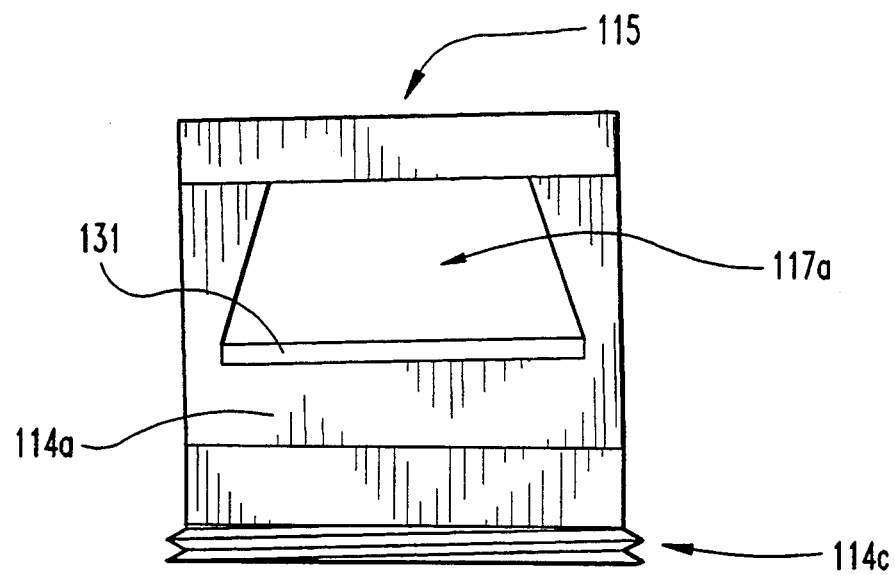
FIG. 19 is an end view of the lateral passage way in the housing according to the present invention to receive the movable member of FIG. 18.
Figure 20:
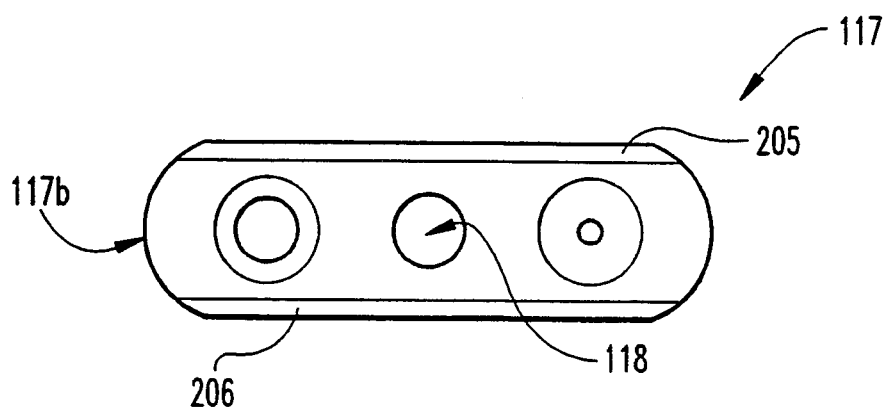
FIG. 20 is an end view of the housing of the device of FIG. 12.

A number of variations are contemplated to be within the scope of applicant's invention and may be included to adapt the device to a particular use without changing the basic features. For example, movable member 117 may optionally be positioned beneath valve 116 instead of above valve 116 as illustrated in the Figures. Moreover, upper housing 114a may have cylindrical side walls surrounding opening 117a as shown in FIG. 19 which corresponds in curvature to the curved end 117b (see FIG. 20) of the movable member. With both such curvatures matching, the operator is assured that the opening in the movable member is aligned with the cannula passageway when the movable member is in a second position the walls are flush (see FIG. 14) giving visual and tactile confirmation of alignment. Therefore, while the invention has been described in detail in the foregoing description of the preferred embodiment, this description is to be considered illustrative and not restrictive in character. It is to be understood that only the preferred embodiments have been shown and described, and that all changes and modifications within the spirit of the invention are desired to be projected.

What is claimed is:

1. A device for a surgical cannula, said surgical cannula having a tubular member defining a passageway insertable into a medical patient and a housing member at a proximal end of the tubular member and adapted to receive a movable member transversely across the passageway of the tubular member, comprising:
    (a) a movable member mountable to the housing cannula and movable transversely across the passageway;
    (b) a first aperture in said movable member;
    (c) a first valve body mountable in said first aperture, said first valve body having an opening sized to receive and provide a fluid tight seal around a first medical device;
    (d) a second aperture in said movable member sized to receive a second medical device, wherein said movable member is transversely movable across the passageway of the cannula between a first position with said first valve body aligned with the passageway and a second position with the second aperture aligned with the passageway.

2. A device according to claim 1 wherein said movable member and said first valve body are surgically sterile.

3. A device according to claim 2 wherein said movable member has an upper surface and a lower surface, said lower surface having a greater surface area than said upper surface.

4. A device according to claim 3 wherein said movable member has a trapezoidally-shaped cross section corresponding in profile to a trapezoidally-shaped transverse opening in the housing for receiving said movable member.

5. A device according to claim 4 wherein said movable member further comprises:
    (e) a third aperture in said movable member;
    (f) a third-aperture valve body mountable in said third aperture, said third-aperture valve body having an opening sized to receive and provide a fluid tight seal around a third medical device with an outer cross-sectional dimension different than the outer cross-sectional dimensions of the first and second medical devices.

6. A device according to claim 1 wherein said movable member has an upper surface and a lower surface, said lower surface having a greater surface area than said upper surface.

7. A device according to claim 1 wherein said movable member has a trapezoidally-shaped cross section corresponding in profile to a trapezoidally-shaped transverse opening in the housing for receiving said movable member.

8. A device according to claim 1 wherein said movable member further comprises:
    (e) a third aperture in said movable member;
    (f) a third-aperture valve body mountable in said third aperture, said third-aperture valve body having an opening sized to receive and provide a fluid tight seal around a third medical device with an outer cross-sectional dimension different than the outer cross-sectional dimensions of the first and second medical devices.

9. A kit for for a surgical cannula, said surgical cannula having a tubular member defining a passageway insertable into a medical patient and a housing member at the proximal end of the tubular member and adapted to receive a member transversely movable across the passageway of the tubular member; said kit comprising:
    (a) a movable member mountable to the housing cannula and movable transversely across the passageway, said movable member having a first aperture therein and further having a second aperture therein;
    (b) at least one valve body mountable in at least one of said apertures, said valve body having an opening sized to receive and provide a fluid tight seal around a first medical device; and,
    (c) a separate elastomeric valve body for mounting in the housing to provide a fluid tight seal across the cannula passageway when no medical devices are inserted therethrough.

10. A kit according to claim 9 wherein said movable member includes an upper surface and a lower surface, said lower surface having a greater surface area than said upper surface.

11. A kit according to claim 10 wherein said movable member has a trapezoidally-shaped cross section corresponding in profile to a trapezoidally-shaped transverse opening in the housing for receiving said movable member.

12. A kit according to claim 11 wherein said movable member further has a third aperture therein, and further comprising:
    (d) a second valve body mountable in at least one of said apertures, said second valve body laving an opening sized to receive and provide a fluid tight seal around a different sized medical device.

13. A kit according to claim 8 wherein said movable member has a trapezoidally-shaped cross section corresponding in profile to a trapezoidally-shaped transverse opening in the housing for receiving said movable member.

14. A kit according to claim 8 wherein said movable member further has a third aperture therein, and further comprising:
    (d) a second valve body mountable in at least one of said apertures, said second valve body having an opening sized to receive and provide a fluid tight seal around a different sized medical device.

15. A device for a surgical cannula, said surgical cannula having a tubular member defining a passageway insertable into a medical patient, comprising:
    (a) a housing member mountable to the proximal end of the tubular member, said housing member having a passageway allowing insertion of a medical device therethrough and into said lumen, said housing member further adapted to receive a movable member transversely across said passageway;

(b) a movable member mountable to the housing member and movable transversely across the passageway;

(c) a first aperture in said movable member;

(d) a first valve body mountable in said first aperture, said first valve body having an opening sized to receive and provide a fluid tight seal around a first medical device;

(e) a second aperture in said movable member sized to receive a second medical device, wherein said movable member is transversely movable across the passageway of the cannula between a first position with said first valve body aligned with the passageway and a second position with the second aperture aligned with the passageway.

16. A device according to claim 15 wherein said housing member and said movable member and said first valve body are surgically sterile.

17. A device according to claim 16 wherein said housing member has means for mounting to the proximal end of said cannula.

18. A device according to claim 17 wherein said housing member has a trapezoidally-shaped transverse opening therein, and wherein said movable member has a trapezoidally-shaped cross section corresponding in profile to said trapezoidally-shaped transverse opening in the housing for receiving said movable member.

19. A device according to claim 18 wherein said movable member further comprises:

(f) a third aperture in said movable member;

(g) a third-aperture valve body mountable in said third aperture, said third-aperture valve body having an opening sized to receive and provide a fluid tight seal around a third medical device with an outer cross-sectional dimension different than the outer cross-sectional dimensions of the first and second medical devices.

20. A device according to claim 15 wherein said housing member has means for mounting to the proximal end of said cannula.

21. A device according to claim 15 wherein said housing member has a trapezoidally-shaped transverse opening therein, and wherein said movable member has a trapezoidally-shaped cross section corresponding in profile to said trapezoidally-shaped transverse opening in the housing for receiving said movable member.

22. A device according to claim 15 wherein said movable member further comprises:

(f) a third aperture in said movable member;

(g) a third-aperture valve body mountable in said third aperture, said third-aperture valve body having an opening sized to receive and provide a fluid tight seal around a third medical device with an outer cross-sectional dimension different than the outer cross-sectional dimensions of the first and second medical devices.

23. A kit according to claim 8 wherein said movable member, said mountable valve body, and said separate elastomeric valve body in the kit are surgically sterile.

* * * * *

UNITED STATES PATENT AND TRADEMARK OFFICE
CERTIFICATE OF CORRECTION

PATENT NO.  : 5,350,362
DATED       : September 27, 1994
INVENTOR(S) : Albert E. Stouder, Jr.

It is certified that error appears in the above-indentified patent and that said Letters Patent is hereby corrected as shown below:

Column 5, line 36, "time" should read —the—.

Column 8, line 43, "time" should read —the—.

Signed and Sealed this

Twentieth Day of December, 1994

Attest:

BRUCE LEHMAN

Attesting Officer     Commissioner of Patents and Trademarks